US00PP37804P2

(12) United States Plant Patent
Mousa

(10) Patent No.: US PP37,804 P2
(45) Date of Patent: Oct. 20, 2026

(54) ***DAHLIA* PLANT NAMED 'Dodahsubesabic'**

(50) Latin Name: *Dahlia variabilis*
Varietal Denomination: DODAHSUBESABIC

(71) Applicant: DUMMEN GROUP B.V., De Lier (NL)

(72) Inventor: Rami Mousa, Bilthoven (NL)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 19/577,102

(22) Filed: Mar. 24, 2026

(51) Int. Cl.
*A01H 5/02* (2018.01)
*A01H 6/14* (2018.01)

(52) U.S. Cl.
USPC ..... Plt./321
CPC ..... *A01H 6/144* (2018.05)

(58) Field of Classification Search
USPC ..... Plt./321
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Dahlia* plant named 'Dodahsubesabic', characterized by its upright and uniformly mounding plant habit; moderately vigorous growth habit and moderate growth rate; freely branching habit; dense and bushy appearance; dark green-colored leaves; early and freely flowering habit; single-type inflorescences with red and orange bi-colored ray florets; and good postproduction longevity.

1 Drawing Sheet

Botanical designation: *Dahlia variabilis*.
Cultivar denomination: 'DODAHSUBESABIC'.

REFERENCED TO RELATED APPLICATION

A European Community Plant Breeder's Rights application for the instant plant was filed by the Applicant/Assignee, Dümmen Group B.V. of De Lier, The Netherlands on Oct. 18, 2024, application number 2024/2428 and published on Dec. 15, 2024. Foreign priority is not claimed to this application.

BACKGROUND OF THE INVENTION

The present invention relates to a new and distinct cultivar of *Dahlia* plant, botanically known as *Dahlia variabilis* and hereinafter referred to by the name 'Dodahsubesabic'.

The new *Dahlia* plant is a product of a planned breeding program conducted by the Inventor in De Lier, The Netherlands. The objective of the breeding program is to create new container *Dahlia* plants that have a freely branching and flowering habit, strong leaves, large attractive inflorescences and good postproduction longevity.

The new *Dahlia* plant originated from a cross-pollination conducted by the Inventor during the autumn of 2021 in De Lier, The Netherlands of a proprietary selection of *Dahlia variabilis* identified as code number DA-1104, not patented, as the female, or seed, parent with a proprietary selection of *Dahlia variabilis* identified as code number DA19-K0182, not patented, as the male, or pollen, parent. The new *Dahlia* plant was discovered and selected by the Inventor as a single flowering plant from within the progeny of the stated cross-pollination in a controlled greenhouse environment in De Lier, The Netherlands during the summer of 2022.

Asexual reproduction of the new *Dahlia* plant by vegetative terminal cuttings in a controlled greenhouse environment in De Lier, The Netherlands since the summer of 2022 has shown that the unique features of this new *Dahlia* plant are stable and reproduced true to type in successive generations.

SUMMARY OF THE INVENTION

Plants of the new *Dahlia* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Dodahsubesabic'. These characteristics in combination distinguish 'Dodahsubesabic' as a new and distinct *Dahlia* plant:

1. Upright and uniformly mounding plant habit.
2. Moderately vigorous growth habit and moderate growth rate.
3. Freely branching habit; dense and bushy appearance.
4. Dark green-colored leaves.
5. Early and freely flowering habit.
6. Single-type inflorescences with red and orange bi-colored ray florets.
7. Good postproduction longevity.

Compared to plants of the female parent selection, plants of the new *Dahlia* differ primarily in ray floret color as inflorescences of plants of the new *Dahlia* have red and orange bi-colored ray florets whereas inflorescences of plants of the female parent selection have red-colored ray florets. In addition, plants of the new *Dahlia* are more compact than plants of the female parent selection.

Compared to plants of the male parent selection, plants of the new *Dahlia* differ primarily in ray floret color as inflorescences of plants of the new *Dahlia* have red and orange bi-colored ray florets whereas inflorescences of plants of the male parent selection have white and purple bi-colored ray florets. In addition, plants of the new *Dahlia* are more compact than plants of the male parent selection.

Plants of the new *Dahlia* can be compared to plants of *Dahlia* sp. 'Dodasumberebic', disclosed in U.S. Plant Pat. No. 36,635. In side-by-side comparisons, plants of the new *Dahlia* differ primarily from plants of 'Dodasumberebic' in the following characteristics:

1. Plants of the new *Dahlia* are more compact than plants of 'Dodasumberebic'.
2. Ray florets of plants of the new *Dahlia* are red and orange bi-colored whereas ray florets of plants of 'Dodasumberebic' are bright red and yellow bi-colored.

BRIEF DESCRIPTION OF THE PHOTOGRAPH

The accompanying photograph illustrates the overall appearance of the new *Dahlia* plant showing the colors as true as it is reasonably possible to obtain in colored reproductions of this type. Colors in the photograph may differ slightly from the color values cited in the detailed botanical description which accurately describe the colors of the new *Dahlia* plant. The photograph is a side perspective view of a typical flowering plant of 'Dodahsubesabic' grown in a container.

DETAILED BOTANICAL DESCRIPTION

The aforementioned photograph and the following observations and measurements describe plants grown during the spring in 15-cm containers in a glass-covered greenhouse in De Lier, The Netherlands and under environmental conditions and cultural practices which approximate those generally used in commercial potted *Dahlia* production. During the production of the plants, day temperatures ranged from 18° C. to 30° C., night temperatures ranged from 16° C. to 22° C. and light levels were at a minimum 135 watt/m$^2$. Plants were pinched one time about four weeks after sticking unrooted cuttings. Plants were eleven weeks old when the photograph and the detailed description were taken. In the following description, color references are made to The Royal Horticultural Society Colour Chart, Fifth Edition, except where general terms of ordinary dictionary significance are used.

Botanical classification: *Dahlia variabilis* 'Dodahsubesabic'.

Parentage:

*Female, or seed, parent*.—Proprietary selection of *Dahlia variabilis* identified as code number DA-1104, not patented.

*Male, or pollen, parent*.—Proprietary selection of *Dahlia variabilis* identified as code number DA19-K0182, not patented.

Propagation:

*Type*.—By vegetative terminal cuttings.

*Time to initiate roots, summer*.—About twelve days at temperatures about 22° C. to 30° C.

*Time to initiate roots, winter*.—About 14 days at temperatures about 20° C. to 22° C.

*Time to produce a rooted plant, summer*.—About 21 days at temperatures about 22° C. to 30° C.

*Time to produce a rooted plant, winter*.—About 24 days at temperatures about 20° C. to 22° C.

*Root description*.—Medium in thickness, fibrous; typically whitish grey in color, actual color of the roots is dependent on substrate composition, water quality, fertilizers, substrate temperature and age of roots; tuber development has not been observed on plants of the new *Dahlia*.

*Rooting habit*.—Moderately freely branching; medium density.

Plant description:

*Plant and growth habit*.—Upright and uniformly mounding plant form; overall shape, globular; freely basal branching habit with about three primary lateral branches per plant, each primary lateral branch with about three secondary lateral branches; dense and bushy appearance; pinching is not required, but will enhance lateral branch development; inflorescences held above the foliar plane on sturdy peduncles; moderately vigorous growth habit and moderate growth rate.

*Plant height, soil level to top of foliar plane*.—About 20.5 cm.

*Plant height, soil level to top of floral plane*.—About 30 cm.

*Plant diameter or spread*.—About 32 cm.

*Lateral branches*.—Length: About 24 cm. Diameter: About 6 mm. Internode length: About 2 cm to 4.5 cm. Aspect: Erect to about 20° from vertical. Strength: Sturdy. Texture and luster: Smooth, glabrous; semi-glossy. Color, developing and developed: Close to 144A.

Leaf description:

*Arrangement*.—Opposite; single, not compound.

*Length*.—About 15 cm.

*Width*.—About 7 cm to 8 cm.

*Shape*.—Rhomboid.

*Apex*.—Acute.

*Base*.—Attenuate.

*Margin*.—Dentate.

*Venation pattern*.—Pinnate.

*Texture and luster, upper and lower surfaces*.—Smooth, glabrous; matte.

*Color*.—Developing leaves, upper surface: Close to 146A. Developing leaves, lower surface: Close to 191A. Fully expanded leaves, upper surface: Close to 147A; venation, close to 147D. Fully expanded leaves, lower surface: Close to 191A; venation, close to 146D.

*Petioles*.—Length: About 4.2 cm. Diameter: About 3 mm. Strength: Sturdy. Texture and luster, upper and lower surfaces: Smooth, glabrous; semi-glossy. Color, upper and lower surfaces: Close to 144B.

Inflorescence description:

*Appearance and arrangement*.—Single-type inflorescence form with ray and disc florets forming acropetally on a receptacle; inflorescences positioned above the foliar plane on sturdy peduncles; inflorescences face mostly upright to slightly outwardly; freely flowering habit with about 28 inflorescences developing per plant.

*Fragrance*.—None detected.

*Time to flower*.—Early flowering habit, plants begin flowering about ten to twelve weeks after planting; in the garden in The Netherlands, plants flower continuously from spring until late summer.

*Post-production longevity*.—Depending on temperatures, inflorescences maintain good substance for about two to three weeks on the plant; inflorescences persistent.

*Inflorescence buds*.—Height: About 9 mm. Diameter: About 1.3 cm. Shape: Globular. Texture and luster: Smooth, glabrous; glossy. Color: Close to 144B.

*Inflorescence size*.—Diameter: About 10 cm. Depth (height): About 1.5 cm. Disc diameter: About 2 cm. Receptacle diameter: About 1.5 cm. Receptacle height: About 5 mm. Receptacle color: Close to 144A.

*Ray florets*.—Quantity per inflorescence: About eight arranged in a single whorl. Length: About 4.5 cm. Width: About 2.8 cm. Shape: Elliptic. Apex: Obtuse. Base: Obtuse. Margin: Entire; not undulate. Aspect: Initially upright and with development, outwardly. Texture and luster, upper and lower surfaces: Smooth, glabrous; matte. Color: When opening, upper surface: Proximally, close to 46B; distally close to 26A. When opening, lower surface: Proximally, close to 34C; distally close to 26C. Fully opened, upper surface: Proximally, close to 46C; distally close to 26A; venation, close to 15D; color does not change with subsequent development. Fully opened, lower surface: Proximally, close to 18B; distally close to 14D; venation, close to 12C; proximal color becoming closer to 18B with subsequent development.

*Disc florets*.—Quantity per inflorescence: About 40 to 50 arranged in about five whorls. Length: About 6 mm. Diameter: About 2 mm. Shape: Tubular, elongated; apices acute. Texture and luster: Smooth, glabrous; glossy. Color, when opening and fully opened, inner and outer surfaces: Close to 9A; venation, close to 9A.

*Phyllaries*.—Quantity per inflorescence: About eight arranged in a single whorl. Length: About 2 cm. Width: About 7 mm. Shape: Oblong. Apex: Rounded acute. Base: Truncate. Margin: Entire. Texture and luster, upper and lower surfaces: Smooth, glabrous; semi-glossy. Color, upper and lower surfaces: Distally, close to 145B and proximally, close to 144A.

*Peduncles*.—Length, terminal peduncle: About 4.5 cm. Diameter, terminal peduncle: About 4 mm. Aspect: Mostly erect to slightly outwardly. Strength: Sturdy. Texture and luster: Smooth, glabrous; semi-glossy. Color: Close to 144A.

*Reproductive organs*.—Androecium: Present on disc florets only. Stamen quantity per floret: Five. Filament length: About 8 mm. Filament color: Close to 150D. Anther length: About 4 mm. Anther color: Close to 17B. Pollen amount: Moderate. Pollen color: Close to 23A. Gynoecium: Present on disc florets only. Pistil quantity per floret: One. Pistil length: About 1 cm. Style length: About 8 mm. Style color: Close to 150C. Stigma diameter: About 0.5 mm. Stigma shape: Bifurcate. Stigma color: Close to 17A. Ovary color: Close to 158D. Seeds: To date, seed development has not been observed on plants of the new *Dahlia*.

Pathogen & pest resistance: To date, plants of the new *Dahlia* have not been observed to be resistant to pathogens and pests common to *Dahlia* plants.

Temperature tolerance: Plants of the new *Dahlia* tolerate temperatures from about 10° C. to 35° C.

It is claimed:

1. A new and distinct *Dahlia* plant named 'Dodahsubesabic' as herein illustrated and described.

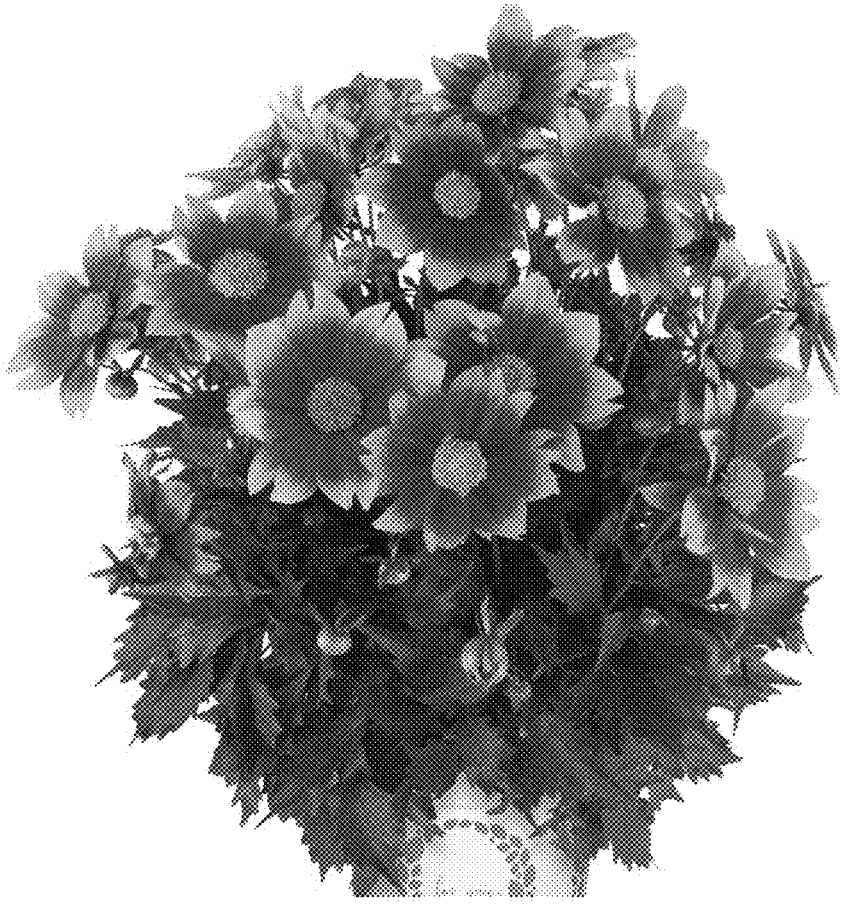

* * * * *